(12) United States Patent
Chua

(10) Patent No.: US 10,413,469 B2
(45) Date of Patent: Sep. 17, 2019

(54) UNIVERSAL TRENDELENBURG POSITIONER

(75) Inventor: Mark Spencer G. Chua, Northbrook, IL (US)

(73) Assignee: Medline Industries, Inc., Northfield, IL (US)

( * ) Notice: Subject to any disclaimer, the term of this patent is extended or adjusted under 35 U.S.C. 154(b) by 1827 days.

(21) Appl. No.: 13/489,811

(22) Filed: Jun. 6, 2012

(65) Prior Publication Data

US 2013/0327339 A1 Dec. 12, 2013

(51) Int. Cl.
| | |
|---|---|
| A61F 5/37 | (2006.01) |
| A61G 13/04 | (2006.01) |
| A61G 13/12 | (2006.01) |
| A61G 7/005 | (2006.01) |
| A61G 7/057 | (2006.01) |

(52) U.S. Cl.
CPC ......... *A61G 13/04* (2013.01); *A61G 13/1255* (2013.01); *A61F 5/3784* (2013.01); *A61G 7/005* (2013.01); *A61G 7/057* (2013.01); *A61G 2203/46* (2013.01); *A61G 2210/90* (2013.01)

(58) Field of Classification Search
CPC ........ A61F 5/3769; A61F 5/37; A61F 5/3776; A61F 5/3784; A61G 7/05; A61G 7/0504; A47C 21/08
USPC ............. 128/105.1, 849, 853, 869, 874–876; 5/621, 622–624, 635; 2/459, 461–462, 2/467, 44–45; 606/237
See application file for complete search history.

(56) References Cited

U.S. PATENT DOCUMENTS

| | | | | |
|---|---|---|---|---|
| 2,845,314 A | * | 7/1958 | Long ..................... | A61F 5/3784 5/601 |
| 3,265,065 A | * | 8/1966 | Jillson ................... | A61F 5/3784 128/874 |
| 3,297,026 A | * | 1/1967 | Van Pelt ............... | A61F 5/3761 128/878 |
| 4,068,314 A | * | 1/1978 | Yellen ................ | A41D 13/0012 2/94 |
| 4,331,161 A | * | 5/1982 | Patel ........................ | A61B 5/01 600/22 |
| 4,742,821 A | * | 5/1988 | Wootan .................. | A61F 5/3776 128/873 |

(Continued)

OTHER PUBLICATIONS

"Website—Publication", *AliMed*; AliMed.com; Butterfly Steep Trendelenburg Bean Bag Positioner with Gel published 2012.

(Continued)

*Primary Examiner* — Kari K Rodriquez
*Assistant Examiner* — Camtu T Nguyen
(74) *Attorney, Agent, or Firm* — Philip H. Burrus, IV

(57) ABSTRACT

A patient positioner (100) includes a central portion (102) and a pair of shoulder restraints (105,106) extending distally away from a first side (107) of the central portion. Each shoulder restraint can terminate at an attachment area (108, 109). Each attachment area can comprise fastener (114,115). Complementary fasteners (214,215) can be disposed on the central portion (102). The shoulder restraints can then be folded (116) about a patient's shoulders, with the fasteners attaching to the complementary fasteners. A plurality of securement straps (121,122,123,124,125,126) configured to attach the patient positioner to a procedure table (701) can extend distally from the second side (110) and the third side (111) of the central portion, respectively.

17 Claims, 11 Drawing Sheets

(56) References Cited

U.S. PATENT DOCUMENTS

| | | | |
|---|---|---|---|
| 4,848,793 A * | 7/1989 | Huspen | 280/801.1 |
| 6,053,580 A * | 4/2000 | White, Sr. | B60R 22/14 |
| | | | 297/467 |
| 6,622,324 B2 | 9/2003 | VanSteenburg et al. | |
| 7,516,743 B2 | 4/2009 | Hoffman | |
| 8,162,194 B2 | 4/2012 | Gleason | |
| 2005/0236002 A1 * | 10/2005 | Cooley | A47D 15/008 |
| | | | 128/845 |
| 2009/0095780 A1 | 4/2009 | Wangeby | |
| 2010/0242177 A1 | 9/2010 | Malcolm et al. | |
| 2010/0275377 A1 | 11/2010 | West | |
| 2010/0308086 A1 | 12/2010 | Chapuis | |
| 2011/0047706 A1 | 3/2011 | Hiebert | |
| 2011/0089205 A1 | 4/2011 | Coote | |
| 2012/0024926 A1 | 2/2012 | Ghassemi | |
| 2012/0074190 A1 | 3/2012 | Fisher et al. | |

OTHER PUBLICATIONS

"Website—Publication", *Xodus Medical*; www.xodusmedical.com; "Pigazzi Patient Positioning System" published 2012.

\* cited by examiner

— # UNIVERSAL TRENDELENBURG POSITIONER

BACKGROUND

Technical Field

This invention relates generally to a medical accessory, and more particularly to a patient positioner suitable for use during surgery.

Background Art

During a medical procedure, such as a surgical procedure, a patient is placed on a procedure table. In many procedures, a patient positioner is used to retain the patient in a specific location or position on the procedure table. For example, in some abdominal or other surgical procedures, the tilt angle of the procedure table is changed such that the patient's pelvis is above the head so as to allow gravity to assist in moving organs not involved in the procedure away from the procedure site. Such a position is commonly referred to as the "Trendelenburg" position after the German surgeon Freidrich Trendelenburg. In addition to facilitating the gravitational movement of organs away from the procedure site, the Trendelenburg position provides an advantageous field of view of the surgeon during many procedures. In some procedures, the steeper the angle of tilt, the more effectively the patient is positioned. Some Trendelenburg positions have corresponding tilt angles of forty-five degrees or greater.

When placing a person in the Trendelenburg position, medical practitioners worry about the patient slipping or sliding along the procedure table due to the tilt angle. If a person slips, not only can it affect the procedure, but repositioning the person can require the assistance of multiple people. This problem is complicated by the fact that the patient is generally anesthetized during a surgical procedure, which makes the patient harder to reposition. Repositioning a patient can be tedious, time-consuming and especially hazardous if the surgical operation is well in progress.

There have been many prior art attempts to provide patient positioners that retain the patient on the procedure table when in the Trendelenburg position. Many involve padded barriers placed against the patient's body and held against the procedure table by elongated arms extending from rails. The arms are long and thus create large torque moments. These moments cause locking and other mechanical components to wear and fail. Moreover, these complex solutions require the time-consuming manipulation knobs, levers, and latches. Further, the length, bulkiness, and complexity of the bracing and restraining structures can interfere with a surgeon's access to procedural equipment.

It would be advantageous to have a simplified patient positioner that is easier to use, more comfortable for the patient, and more reliable.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
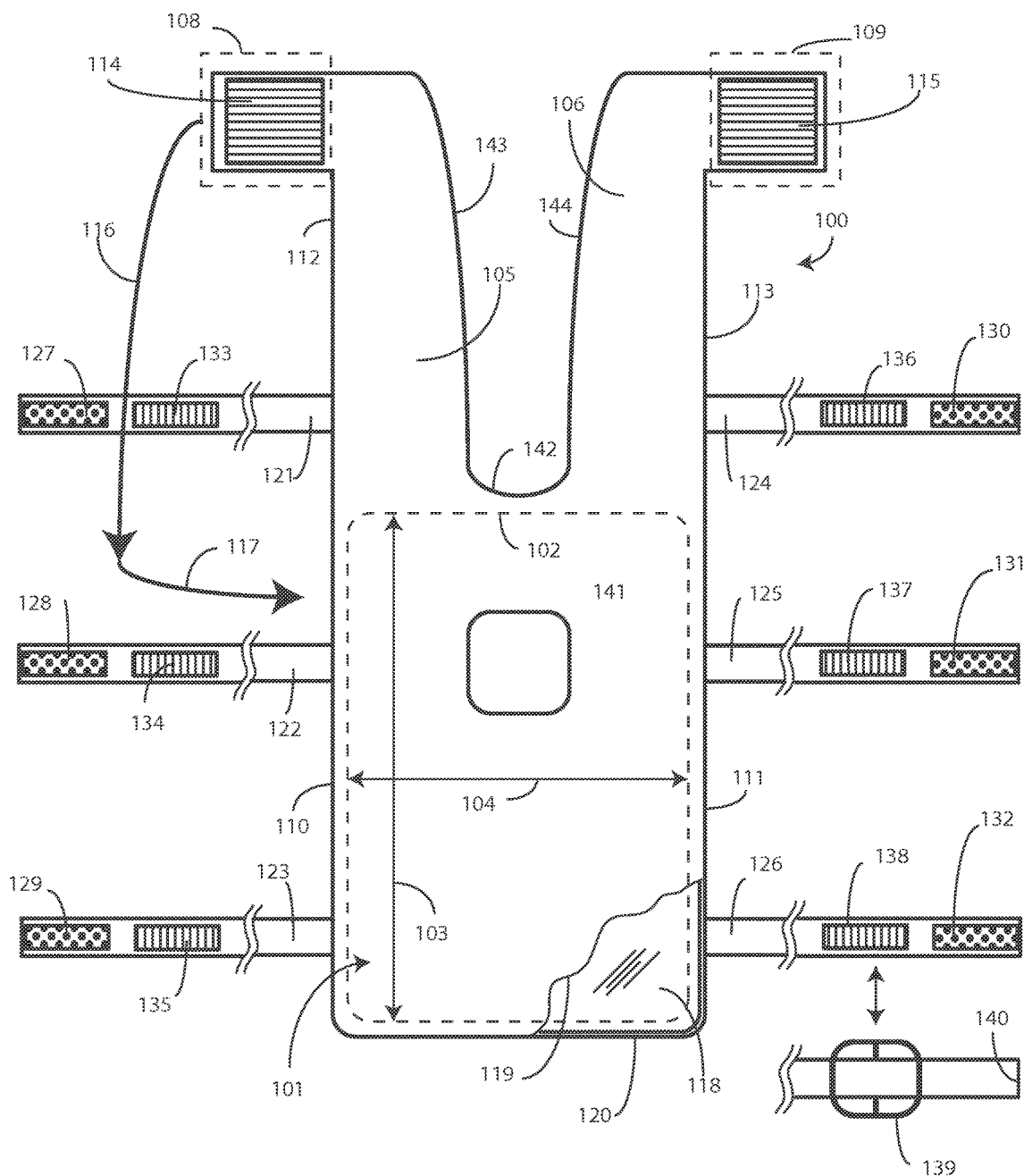
FIG. 1 illustrates a patient-side view of one explanatory patient positioner configured in accordance with one or more embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF EMBODIMENTS OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

Embodiments of the invention provide a simplified system that includes a wearable portion that will retain a patient in the Trendelenburg position quickly, comfortably, and more efficiently that prior art positioners. In one embodiment, the patient positioner includes a central portion and a pair of shoulder restraints extending distally from a first side of the central portion. Each shoulder restraining terminates at an attachment area comprising a fastener. The fastener can be hooks of a hook and loop fastener, loops of a hook and loop fastener, adhesive materials, or other fasteners. Complementary fasteners are then disposed along a second and third side of the central portion, respectively. A patient or medical practitioner affixes the fasteners of the attachment areas to the complementary fasteners by folding a first shoulder restraint about a patient's first shoulder, wrapping a first attachment area about a first edge of the patient positioner to attach it to a side of the patient positioner facing away from the patient's backside. The patient or medical practitioner then folds a second shoulder restraint about a patient's second shoulder, and wraps a second attachment area about a second edge of the patient positioner to attach it to the side of the patient positioner facing away from the patient's backside. Embodiments of the invention form a low profile, unobtrusive, and economical system that helps to retain a patient to a procedure table. Embodiments of the invention are especially useful when a patient is placed in the Trendelenburg position.

Prior art positioners fail to properly distribute the pressure applied by the patient's weight against the positioner when in the Trendelenburg position. Without proper distribution of these forces, it becomes isolated at small, concentrated locations on the patient's body. This concentrated pressure can lead to ulceration of the skin. Embodiments of the present invention work to properly distribute load forces evenly across a patient's shoulders and back, thereby mitigating the risk of ulcer development. Moreover, embodiments of the present invention are unintrusive and easy to place on the patient, thereby saving time and obviating the risk that a surgeon's access to medical equipment will be limited during a procedure.

One significant advantage offered by embodiments of the present invention is that it is designed to work cooperatively with grounding or patient warming systems. When undergoing an operation, patients frequently need to be grounded to facilitate the use of electrical instruments. In many procedures, the patient's body is actually warmed by the procedure table. When heat is applied, a patient warming monitor can be attached to a patient's backside to ensure the thermal level is appropriate. Some embodiments of the present invention define apertures in a central portion that allow a medical practitioner to easily and quickly attach a patient warming monitor through the aperture. Embodiments of the present invention are thus compatible with existing operating room systems.

Figure 2:
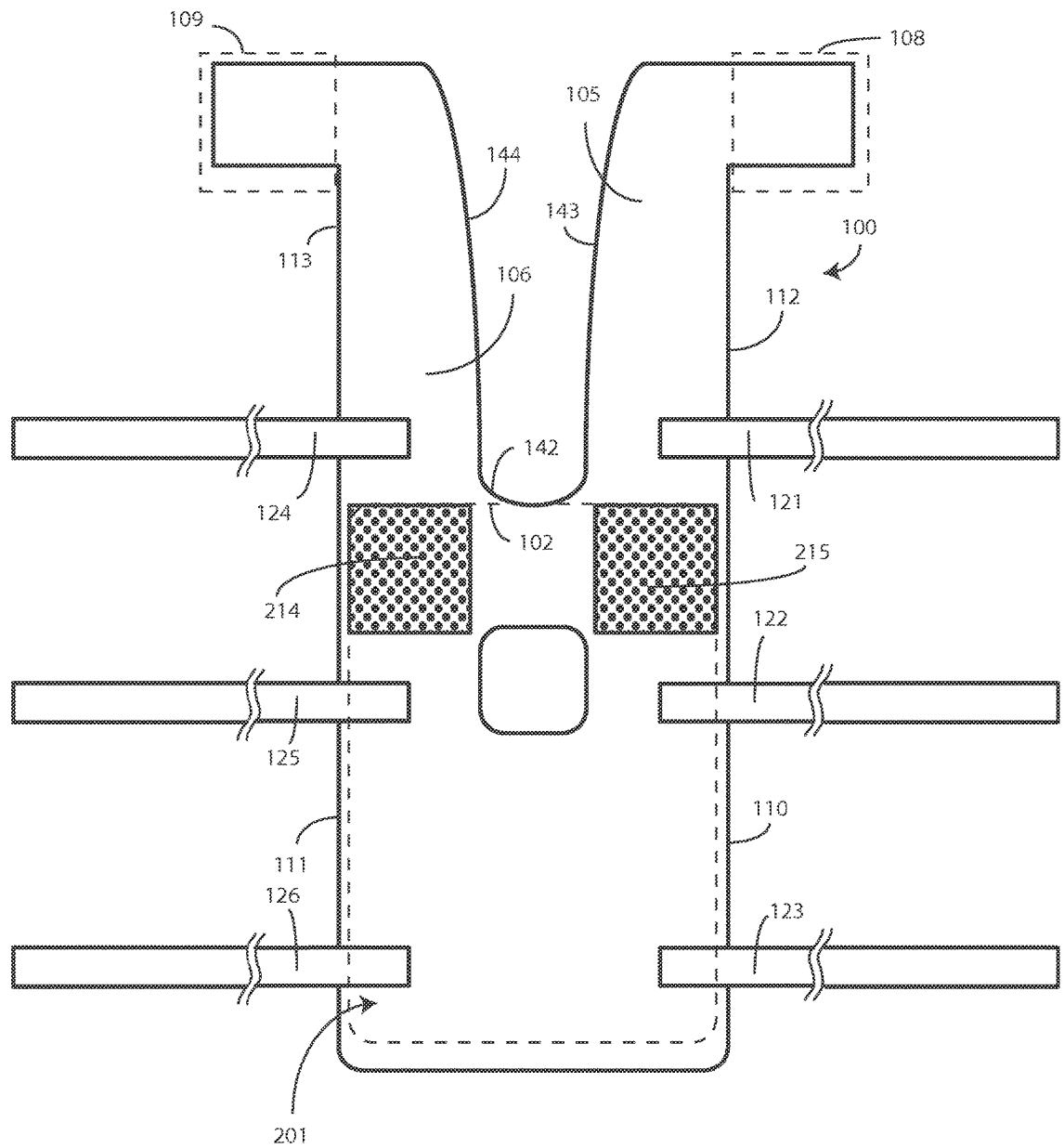
FIG. 2 illustrates a procedure table side view of one explanatory patient positioner configured in accordance with one or more embodiments of the invention.

Turning now to FIGS. 1 and 2, illustrated therein are a patient side 101 and procedure table side 201 of one explanatory patient positioner 100 configured in accordance with one or more embodiments of the invention. FIG. 1 illustrates the "patient side" 101 of the patient positioner 100 because this side will abut the patient's torso when the patient positioner 100 is applied to a patient. Similarly, FIG. 2 illustrates the "procedure table side" 201 of the patient positioner 100 because this side will abut the procedure table when the patient has applied the patient positioner 100 and has been positioned upon the procedure table.

The patient positioner includes a central portion 102. In this illustrative embodiment, the central portion 102 is substantially rectangular in shape. The central portion 102 could take other shapes as well, including ovular shapes, circular shapes, polygonal shapes, and so forth. In one embodiment, the central portion 102 is configured to be substantially rectangular so as to ensure maximum comfort for patients having different sizes and shapes.

In one illustrative embodiment, the central portion 102 has a length 103 of about thirty inches. The term "about" is used to refer to a dimension inclusive of manufacturing tolerances. For example, where the manufacturing tolerance was plus or minus one-half inch, "about thirty inches" could refer to 29.97 or 30.43 inches equally. In one embodiment, the central portion 102 has a width 104 of about twenty inches. Experimental testing has shown that these dimensions allow the patient positioner 100 to comfortably fit a wide range of torso sizes.

A pair of shoulder restraints 105,106 extends distally away from a first side 107 of the central portion 102. In one embodiment, the shoulder restraints 105,106 extend about thirty inches from the first side 107. Each shoulder restraint 105,106 terminates in an attachment area 108,109. In the illustrative embodiment of FIGS. 1 and 2, the attachment areas 108,109 extend distally away from its respective shoulder restraint 105,106 at a substantially orthogonal angle. For example, as shown in FIG. 1 attachment area 108 extends substantially orthogonally away from shoulder restraint 105. Similarly, attachment area 109 extends substantially orthogonally away from shoulder restraint 106.

In addition to defining its first side 107, the central portion 102 also defines a third side 110 and a fourth side 111. In one embodiment, the shoulder restraints 105,106 extend away from the central portion such that a corresponding side 112,113 of each shoulder restraint 105,106 forms an extension of the second side 110 of the central portion 102 and the third side 111 of the central portion 102, respectively. Thus, in this embodiment the side 112 of the first shoulder restraint 105 and the second side 110 form effectively a straight line, while side 113 of the second shoulder restraint 106 and the third side 111 form effectively a straight line. Where this is the case, and the attachment areas 108,109 extend substantially orthogonally away from the shoulder restraints 105, 106, the attachment areas 108,109 will extend substantially orthogonally away from the second side 110 of the central portion 102 and the third side 111 of the central portion 102, respectively.

A pair of fasteners 114,115 is disposed upon the attachment areas 108,109. In the illustrative embodiment of FIGS. 1 and 2, the fasteners 114,115 are disposed along the patient side 101 of the patient positioner 100. In other embodiments, the fasteners 114,115 could be disposed on the procedure table side 201 as well.

In one embodiment, the fasteners 114,115 are either hook or loop fasteners. For example, in the illustrative embodiment of FIGS. 1 and 2 are loops of a hook and loop fastener. In other embodiments, the fasteners 114,115 can comprise adhesive fasteners, mechanical fasteners such as snaps or latches, or other types of fasteners. In the illustrative embodiments of FIGS. 1 and 2, the fasteners 114,115 are the same, i.e., they are both loops of a hook and loop fastener. However, in other embodiments, the fasteners 114,115 could be different.

Another pair of fasteners 214,215 is disposed on the procedure table side 201 of the patient positioner. In the illustrative embodiment of FIG. 2, each of the fasteners 214,215 are disposed along the central portion 102 of the patient positioner 100 just below the shoulder restraints 105,106. However, it will be clear to those of ordinary skill in the art having the benefit of this disclosure that the fasteners 214,215 can be disposed in other locations as well.

In one embodiment, the fasteners 214,215 are complementary to the fasteners 114,115 disposed along the attachment areas 108,109. For example, where the fasteners 114,115 are disposed in the attachment areas 108,109 are loops of a hook and loop system, the fasteners 214,215 disposed on the procedure table side 201 of the patient positioner 100 can be hooks of the hook and loop system. Where the fasteners 114,115 of the attachment areas 108,109 are make snap members, the fasteners 214,215 disposed on the procedure table side 201 of the patient positioner can be female snap members. Where the fasteners 114,115 of the attachment areas 108,109 are half of a zipper, the fasteners 214,215 disposed on the procedure table side 201 of the patient positioner can be other half of the zipper, and so forth.

In use, the shoulder restraints 105,106 are designed to fold 116 along the patient side 101 of the patient positioner 100 about the shoulders of a patient. Once this step is complete, each attachment area 108,109 is then designed to fold 117 about a side of the central portion 102 to allow its corresponding fastener 114,115 to attach to a complementary fastener 214,215 disposed on the patient side 201 of the patient positioner 100. Accordingly, attachment area 108 folds 117 about the second side 110 of the central portion 102 so that fastener 114 can attach to fastener 214. Similarly, attachment area 109 folds about the third side 111 of the central portion 102 so that fastener 115 can attach to fastener 215.

Recall from above that the fasteners 114,115 of the attachment areas 108,109 could be disposed on the procedure table side 201. Where so configured, the complementary fasteners 214,215 could be disposed either on the patient side 101 or the procedure table side 201 of the patient positioner 100. In the former case, the need for a second fold 117 would be eliminated, as the fasteners 114,115 could couple directly to the complementary fasteners 214,215 after the first fold 116. Further, the attachment areas 108,109 would not need to extend orthogonally outward from the shoulder restraints 105,106. In the latter case, the attachment areas 108,109 may be configured to extend substantially orthogonally toward the opposite shoulder restraint 105,106, rather than outwardly away therefrom. The first fold 116 would continue until the attachment areas 108,109 passed by the second side 110 and third side 111, respectively, where the fasteners 114,115 could attach to their complementary fasteners 214,215. Other configurations of attachment areas 108,109, fasteners 114,115, and complementary fasteners 214,215 will be obvious to those of ordinary skill in the art having the benefit of this disclosure.

In one embodiment, one or both of the central portion 102 and shoulder restraints 105,106 are padded. In such an embodiment, a padded layer 118 of foam or other padding material is disposed between two cover layers. In FIG. 1, the cover layers comprise a first layer of material 119 and a second layer of material 120. The padded layer 118 of this illustrative embodiment is sandwiched between the first layer of material 119 and the second layer of material 120. The layers of material 119,120 can be any of a variety of materials, including cotton, nylon, polyester, blends thereof, woven textile materials, or non-woven textile materials. The padded layer 118 is optional, and may not be included in all embodiments. However, the padded layer 118 can add to the comfort of the patient using the patient positioner 100.

In one embodiment, a plurality of securement straps 121,122,123,124,125,126, which are configured to attach the patient positioner 100 to a procedure table, extend distally away from the second side 110 and third side 111 of the central portion 102, respectively. In the illustrative embodiment of FIGS. 1 and 2, three securement straps 121,122,123 extend distally away from the second side 110 of the central portion 102. Similarly, three securement straps 124,125,126 extend distally away from the third side 111 of the central portion 102. The use of six securement straps 121,122,123,124,125,126 is illustrative only. Other numbers of straps can be used as well. Similarly, while the number of securement straps 121,122,123,124,125,126 disposed on each side of the patient positioner 100 is the same in the explanatory embodiment of FIGS. 1 and 2, the number could be different as well. Once side may have more securement straps than another.

In one embodiment, each securement strap 121,122,123, 124,125,126 has attached thereto a fastener. For example, as shown in FIG. 1, each securement strap 121,122,123,124, 125,126 has both a hook fastener 127,128,129,130,131,132 and a loop fastener 133,134,135,136,137,138 attached thereto. The securement straps 121,122,123,124,125,126 can be wrapped around accessory rails of a procedure table. The hook fasteners 127,128,129,130,131,132 can then attach to the loop fasteners 133,134,135,136,137,138 to secure the patient positioner 100 to the procedure table. Where the shoulder restraints 105,106 are wrapped about the shoulders of a patient with the fasteners 114,115 attached to their complementary fasteners 214,215 as described above, the patient will be conveniently and reliably retained in position. This is true even when the table is tilted. Accordingly, the patient positioner 100 of FIGS. 1 and 2 is well suited for use as a Trendelenburg positioner.

Note that while the hook fasteners 127,128,129,130,131, 132 and a loop fasteners 133,134,135,136,137,138 of the securement straps 121,122,123,124,125,126 are one example of a fastener suitable for attaching the patient positioner 100 to a procedure table, others will be obvious to those of ordinary skill in the art having the benefit of this disclosure. Illustrating by example, rather than using hook fasteners 127,128,129,130,131,132 and a loop fasteners 133,134,135,136,137,138, each securement strap 121,122, 123,124,125,126 can comprise a buckle 139. An end 140 of such a securement strap can pass back through the buckle 139 to secure the patient positioner 100 to the procedure table.

In one embodiment, the central portion 102 defines an aperture 141. In the illustrative embodiments of FIGS. 1 and 2, the aperture 141 is specifically configured to serve as a patient warming sensor insertion aperture. Recall from above that the patient side 101 of the patient positioner 100 is configured to abut against a patient's backside when in use. The aperture 141 of this illustrative embodiment is configured to align with the mid-back of the patient to allow a medical professional to insert a patient warming sensor through the aperture 141 for attachment to the patient's back. Prior art patient positioners interfere with such equipment. One primary advantage of embodiments of the present invention over prior art designs is the fact that the patient positioner 100 can be used with existing equipment, including the patient warming sensors that are commonly used in operating room procedures.

Note that when a patient warming system is used, it can be advantageous to configure the central portion 102 to facilitate conduction of heat from the procedure table through the central portion 102 to the patient. Accordingly, in one embodiment where the padded layer 118 is used, the padded layer 118 can be impregnated with a thermally conductive material or otherwise configured to be thermally conductive. In other embodiments, the layers of material 119,120 can be configured to be thermally conductive as well. Some designers will elect to omit the padded layer 118 as another option for more efficiently transferring heat through the central portion 102.

In the illustrative embodiment of FIGS. 1 and 2, each shoulder restraint 105,106 is separated by a concave curvature 142. The concave curvature 142 of this illustrative embodiment is disposed along the first side 102 of the central portion 102 between the shoulder restraints 105,106. While inclusion of this concave curvature 142 is optional, experimental testing has shown that it provides a comfortable neck opening for the patient when the shoulder restraints 105,106 are folded about the shoulders. To provide a uniform, aesthetically pleasing appearance that also provides maximum exposure of the patient's chest when wearing the patient positioner 100, each shoulder restraint 105, 106 comprises an arch 143,144 that extends from the concave curvature 142 to its corresponding attachment area 108,109. Other contours extending from the concave curvature 142 to the attachment areas 108,109 will be obvious to those of ordinary skill in the art having the benefit of this disclosure as well. For example, some medical procedures may require specific portions of the chest to be exposed, which can lead to free-form contours being used along the inner sides of the shoulder restraints 105,106.

Figure 3:
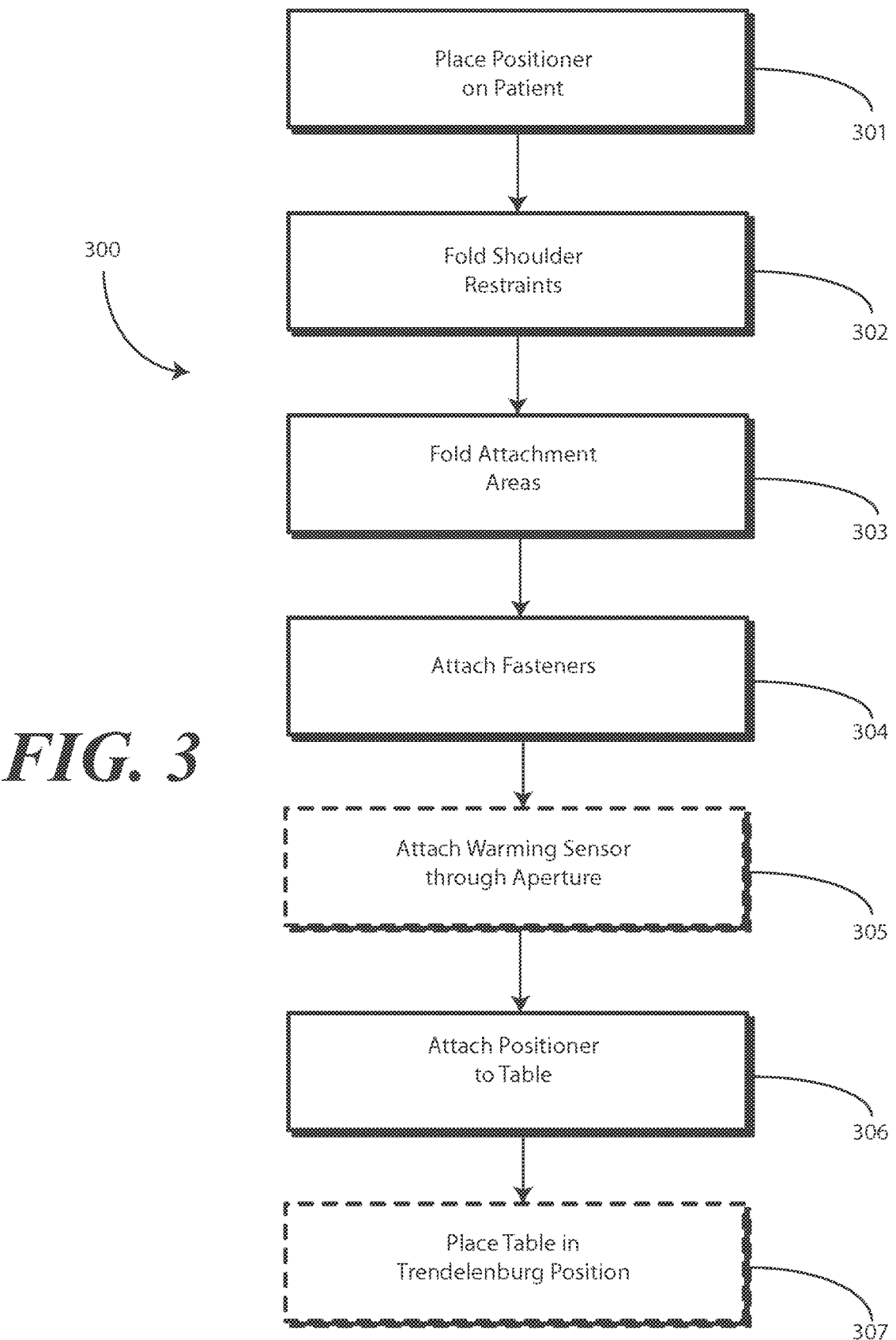
FIG. 3 illustrates one explanatory method of using a patient positioner configured in accordance with one or more embodiments of the invention.

Turning now to FIG. 3, illustrated therein is one explanatory method of using a patient positioner (100) configured as shown in FIGS. 1 and 2. Some of the steps are optional, as are indicated by dashed lines.

At step 301, a medical practitioner or patient first places the patient positioner (100) along the patient's backside. In one embodiment, the central portion (102) of the patient positioner (100) will substantially align with the patient's back such that the aperture (141) falls substantially along the mid-back portion of the patient.

At step 302, the shoulder restraints (105,106) will be wrapped about the patient's shoulders. For example, a first shoulder restraint (105) can be folded (116) about a patient's first shoulder. Similarly, a second shoulder restraint (106) can be folded (116) about the patient's second shoulder.

At step 303, the attachment areas (108,109) of the patient positioner (100) are wrapped about the edges of the central portion (102). Thus, a first attachment area (108) can be wrapped about a second side (110) of the central portion (102) of the patient positioner (100) at this step 303. Similarly, the second attachment area (109) can be wrapped about the third side (111) of the central portion (102) of the patient positioner (100) at this step 303. As described above, this wrapping allows the fasteners (114,115) of the attachment areas (108,109) to attach, at step 304, to the side of the patient positioner (100) facing away from the patient's backside.

Where a patient warming sensor is to be used in a procedure, optional step 305 can include passing the patient warming sensor through an aperture (141) of the central portion (102) and attaching the patient warming sensor to the patient's backside. The patient can then be placed on a procedure table. Using securement straps (121,122,123,124, 125,126), the patient positioner (100) can be attached to the procedure table at step 306. If the procedure to be performed requires the patient to be placed in the Trendelenburg position, this can be done at optional step 307.

Figure 4:
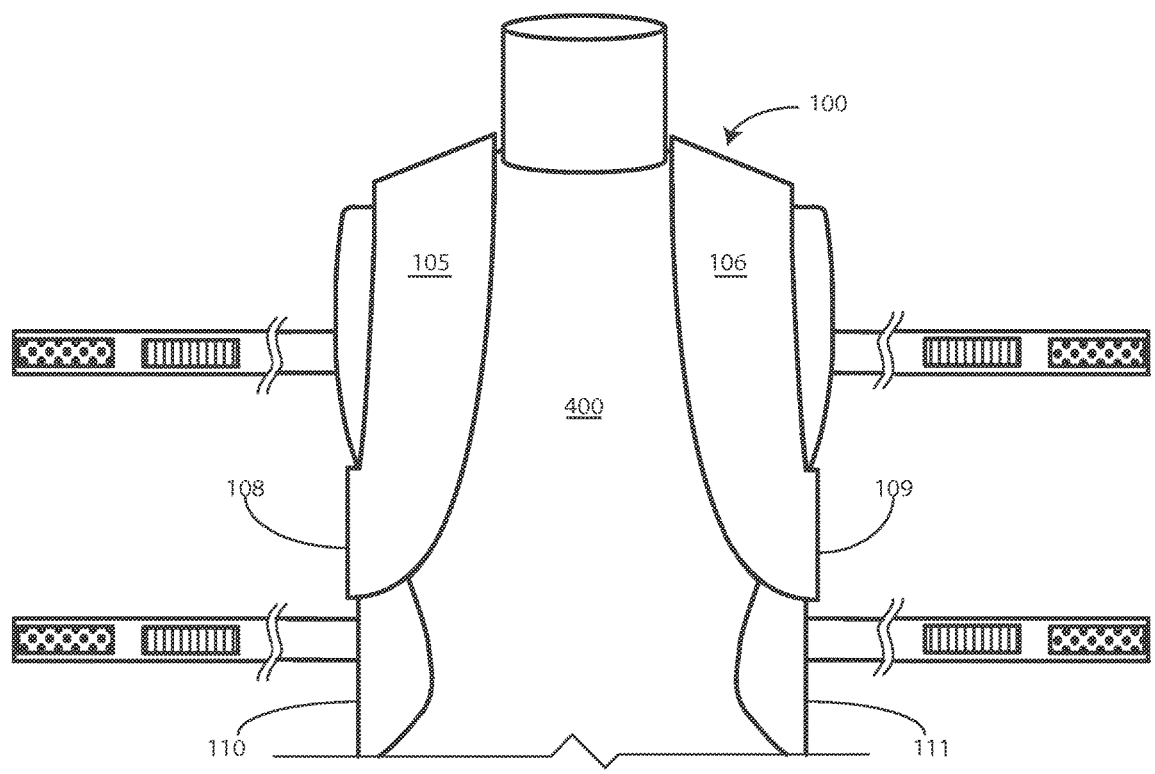
FIG. 4 illustrates a front elevation view of a patient positioner disposed along a patient torso in accordance with the method steps of FIG. 3.
Figure 5:
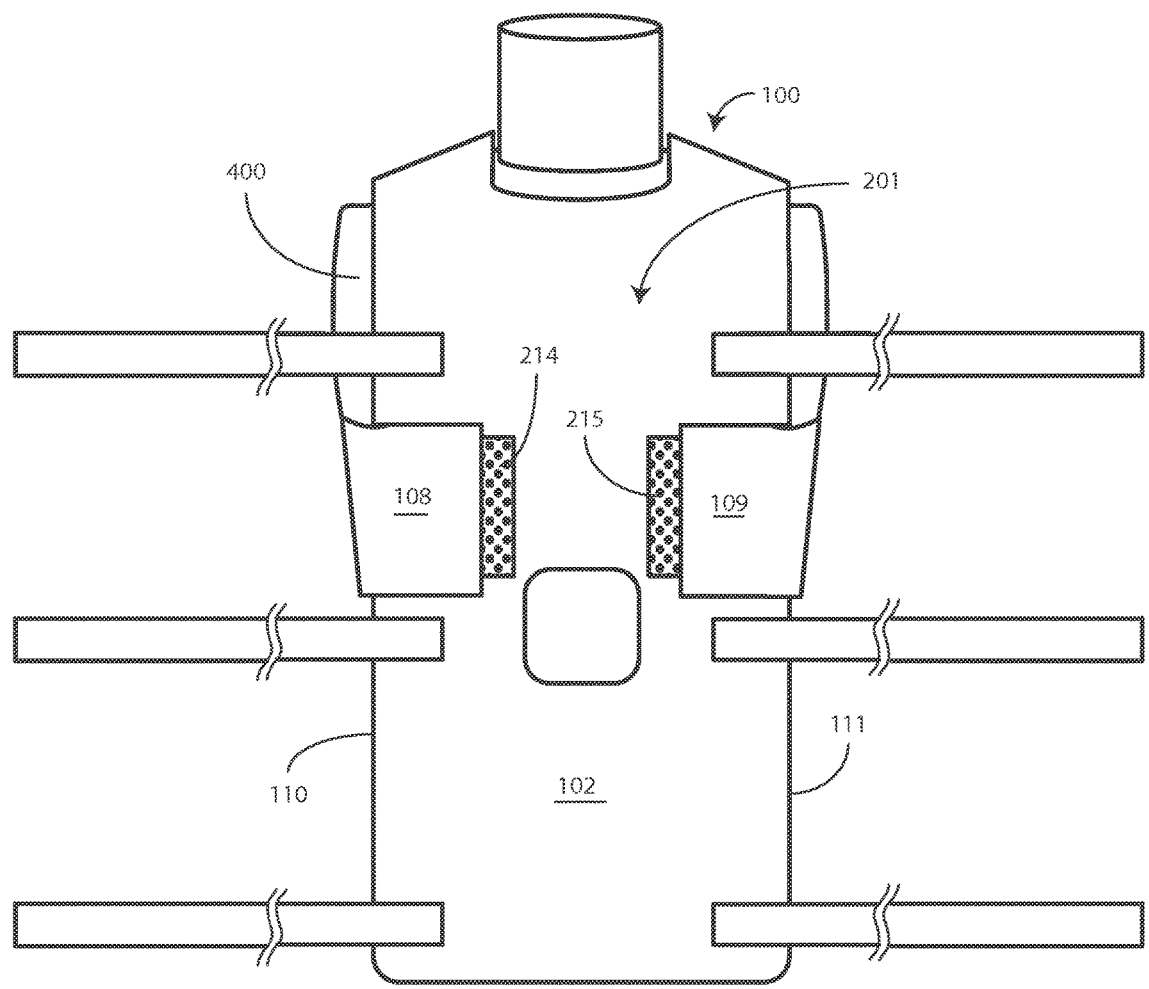
FIG. 5 illustrates a rear elevation view of a patient positioner disposed along a patient torso in accordance with the method steps of FIG. 3.

The result of steps 301,302,303,304 is shown in FIGS. 4 and 5. Turning now to those figures, the patient positioner 100 can be seen after being applied to a patient's torso 400. As shown, the shoulder restraints 105,106 have been folded (116) along the patient side (101) of the patient positioner about the shoulders of the patient. The attachment areas 108,109 have been folded about the second side 110 and third side 111 of the central portion 102 to allow the fasteners (114,115) to attach to the complementary fasteners 214,215 disposed on the procedure table side 201 of the patient positioner 100, which faces away from the patient's backside.

Figure 6:
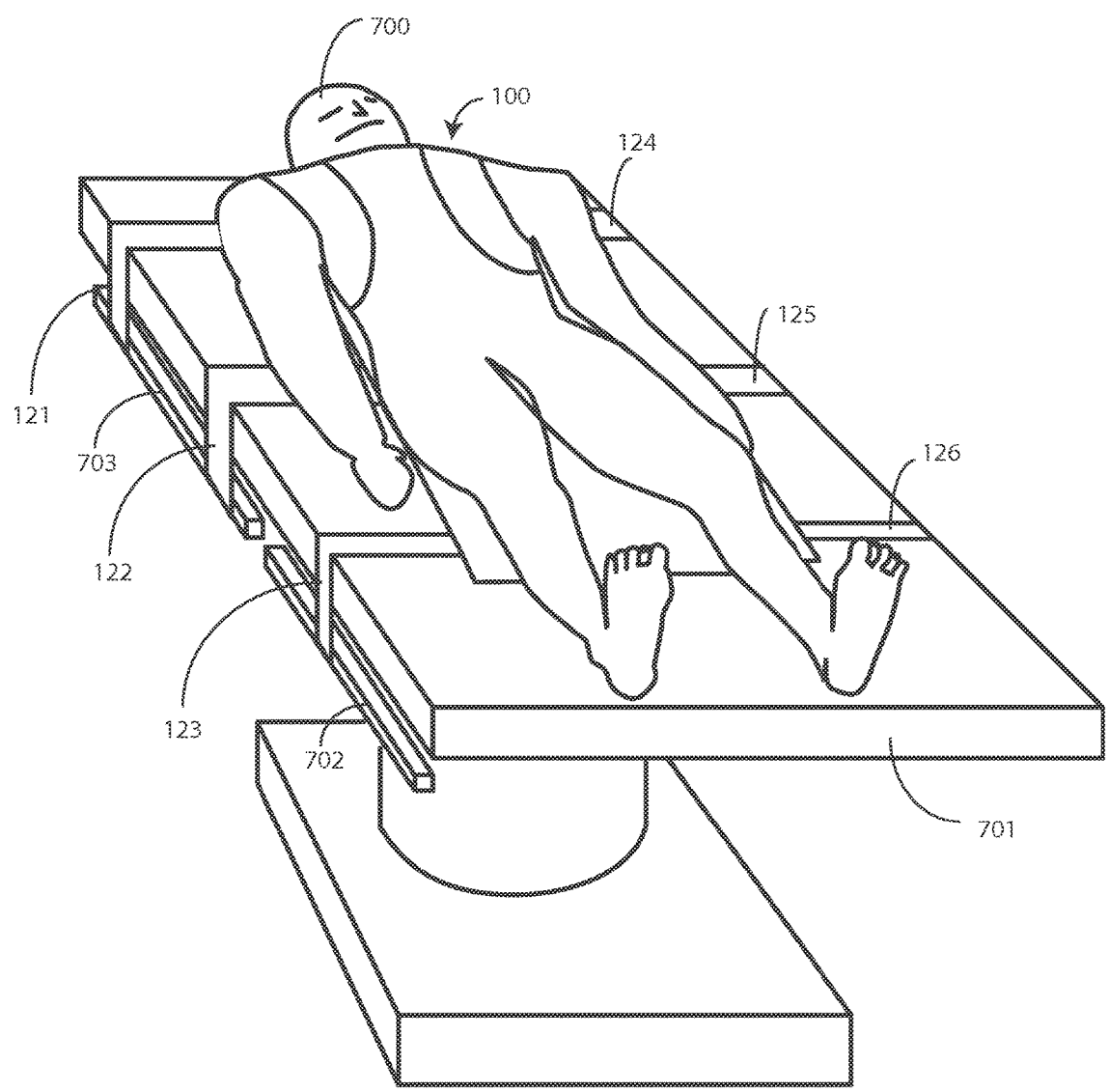
FIG. 6 illustrates a perspective view of a patient on a procedure table being supported by an explanatory patient positioner configured in accordance with one or more embodiments of the invention.
Figure 7:
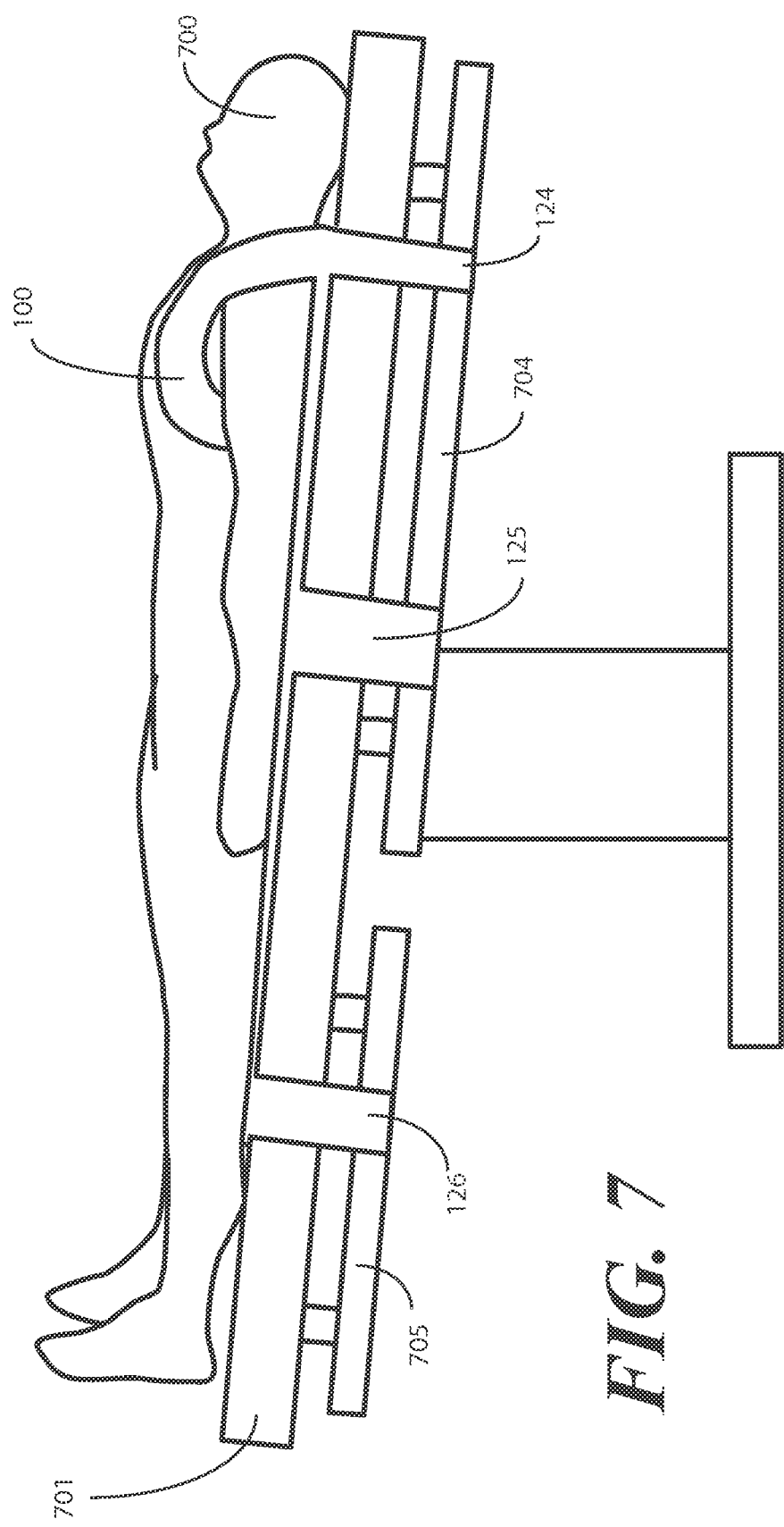
FIG. 7 illustrates a side elevation view of a patient on a procedure table being supported by an explanatory patient positioner configured in accordance with one or more embodiments of the invention.

Once the patient positioner 100 has been donned by the patient, the patient can be positioned on the procedure table. This is shown in FIGS. 6 and 7. Turning now to these figures, a patient 700 wearing a patient positioner 100 is lying on a procedure table 701. The procedure table side (201) of the patient positioner 100 abuts the top surface of the procedure table 701.

To secure the patient positioner 100 to the procedure table 701, the securement straps 121,122,123,124,125,126 have been wrapped about the rails 702,703,704,705 of the procedure table 701. The hook fasteners 127,128,129,130,131, 132 of the securement straps 121,122,123,124,125,126 have been attached to the loop fasteners 133,134,135,136,137,138 to retain the patient positioner 100 securely to the procedure table 701. As shown in FIG. 7, the procedure table has been placed in the Trendelenburg position.

Figure 8:
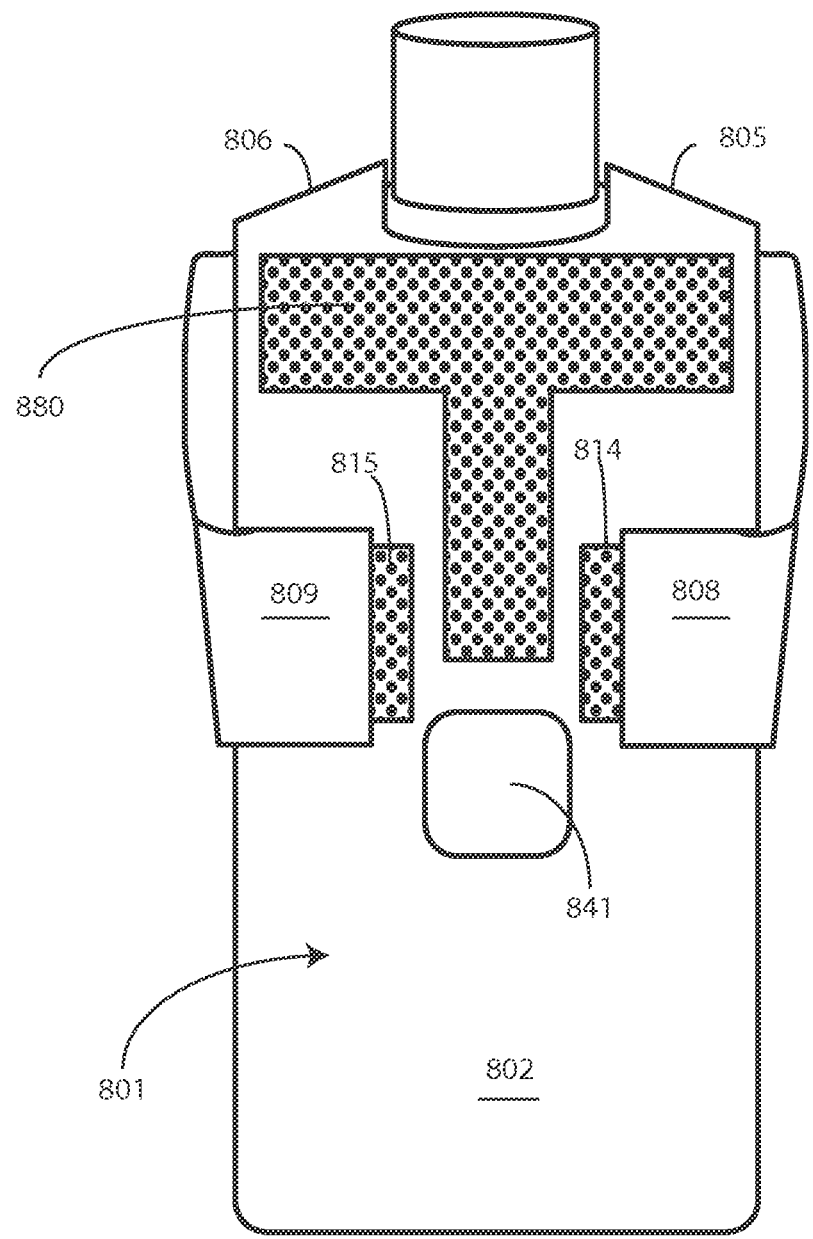
FIG. 8 illustrates a rear elevation view of an alternate patient positioner disposed along a patient torso in accordance with one or more embodiments of the invention.
Figure 9:
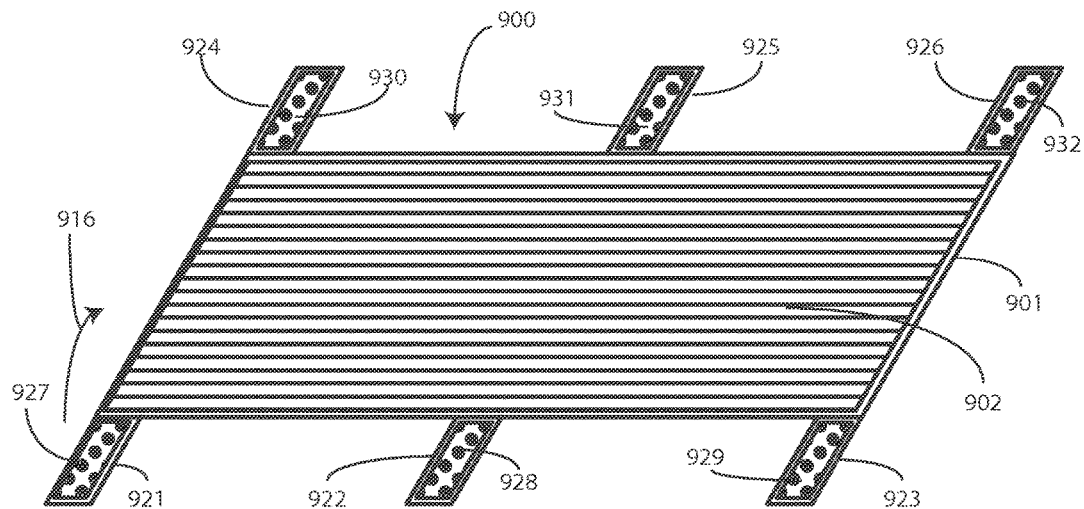
FIG. 9 illustrates one explanatory holding layer configured in accordance with one or more embodiments of the invention.

In some applications, it may be desirous to separate the securement straps 121,122,123,124,125,126 from the patient positioner 100. Turning now to FIGS. 8 and 9, illustrated therein is one such embodiment that does this.

As shown in FIG. 8, the patient positioner 800 is substantially configured as was the patient positioner (100) of FIGS. 1 and 2. However, the patient positioner 800 of FIG. 8 has no securement straps attached thereto. Instead, the patient positioner 800 includes only the wearable portion shown in FIG. 8. A complementary holding layer 900 is shown in FIG. 9.

The wearable portion of FIG. 8 includes many components that are common with the patient positioner (100) of FIGS. 1 and 2. For example, the wearable portion of FIG. 8 includes a central portion 802 having shoulder restraints 805,806 extending distally therefrom in a first direction. As with FIGS. 1 and 2, the shoulder restraints 805,806 are arranged as a pair, with each shoulder restraint 805,806 comprising one of hook or loop fasteners affixed to a patient side of attachment portions 808,809. Another of the hook or loop fasteners 814,815 is disposed on the central portion 802 on a procedure table side 801, which is opposite the side to which the hook or loop fasteners attached to the attachment portions 808,809 are disposed. The central portion 802 also defines a patient warming sensor insertion aperture 841.

Rather than having securement straps, the wearable portion includes an area of fastener material 880 affixed to the central portion 802 on the procedure table side 801 of the patient positioner 800. In this illustrative embodiment, the area of fastener material 880 comprises hook fasteners.

As shown in FIG. 9, the securement straps 921,922,923, 924,925 extend from a holding layer 900. The holding layer 900 includes a table covering portion 901. In this illustrative embodiment, the table covering portion 901 has disposed thereon another area of fastener material 902 that is complementary to the area of fastener material 880 attached to the wearable portion. In this illustrative embodiment, the another area of fastener material 902 comprises loop fasteners. As with previous embodiments, hook and loop fasteners are illustrative only. Adhesive, mechanical, or other fasteners could be substituted.

Since the another area of fastener material 902 is configured as loop fasteners, in this illustrative embodiment each securement strap 921,922,923,924,925,926 has hook fasteners 927,928,929,930,931,932 attached on a side common with the another area of fastener material 902. Accordingly, the securement straps 921,922,923,924,925,926 can be folded 916 back across the table covering portion 901 to attach to the another area of fastener material 902.

Figure 10:
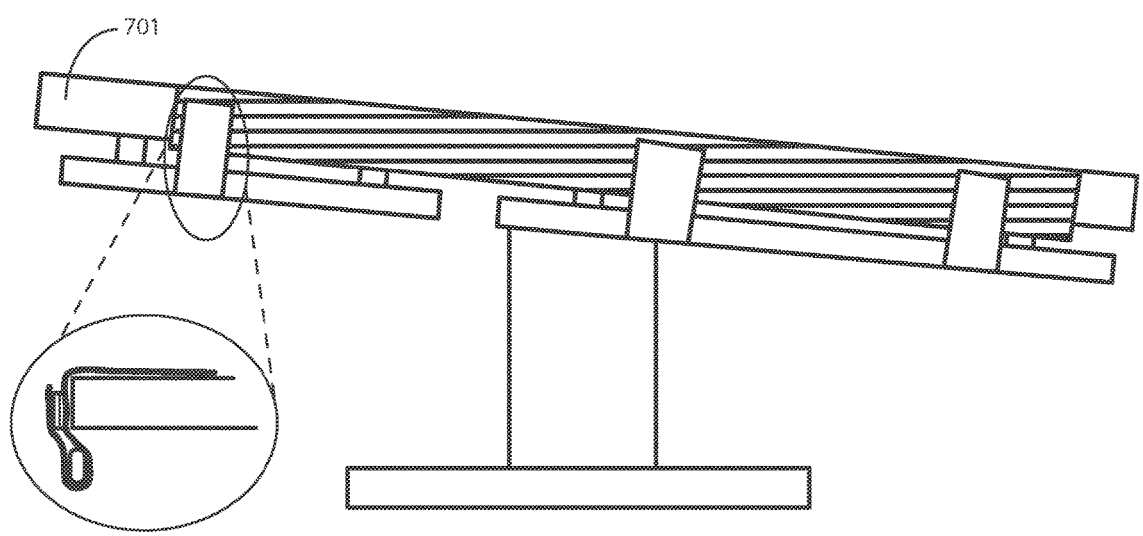
FIG. 10 illustrates one explanatory holding layer disposed along a procedure table in accordance with one or more embodiments of the invention.
Figure 11:
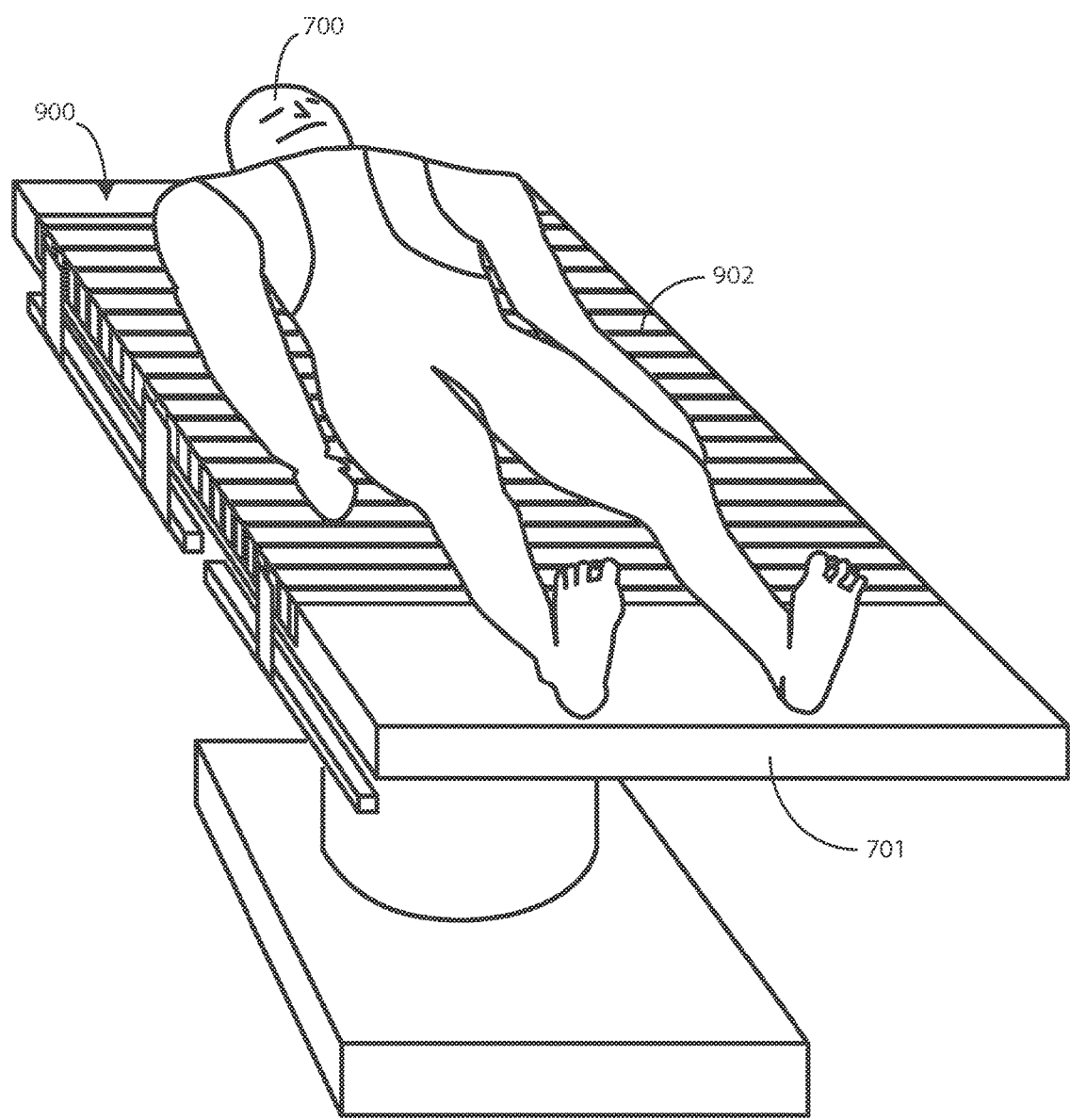
FIG. 11 illustrates a perspective view of a patient on a procedure table being supported by an explanatory patient positioner configured in accordance with one or more embodiments of the invention.
Figure 12:
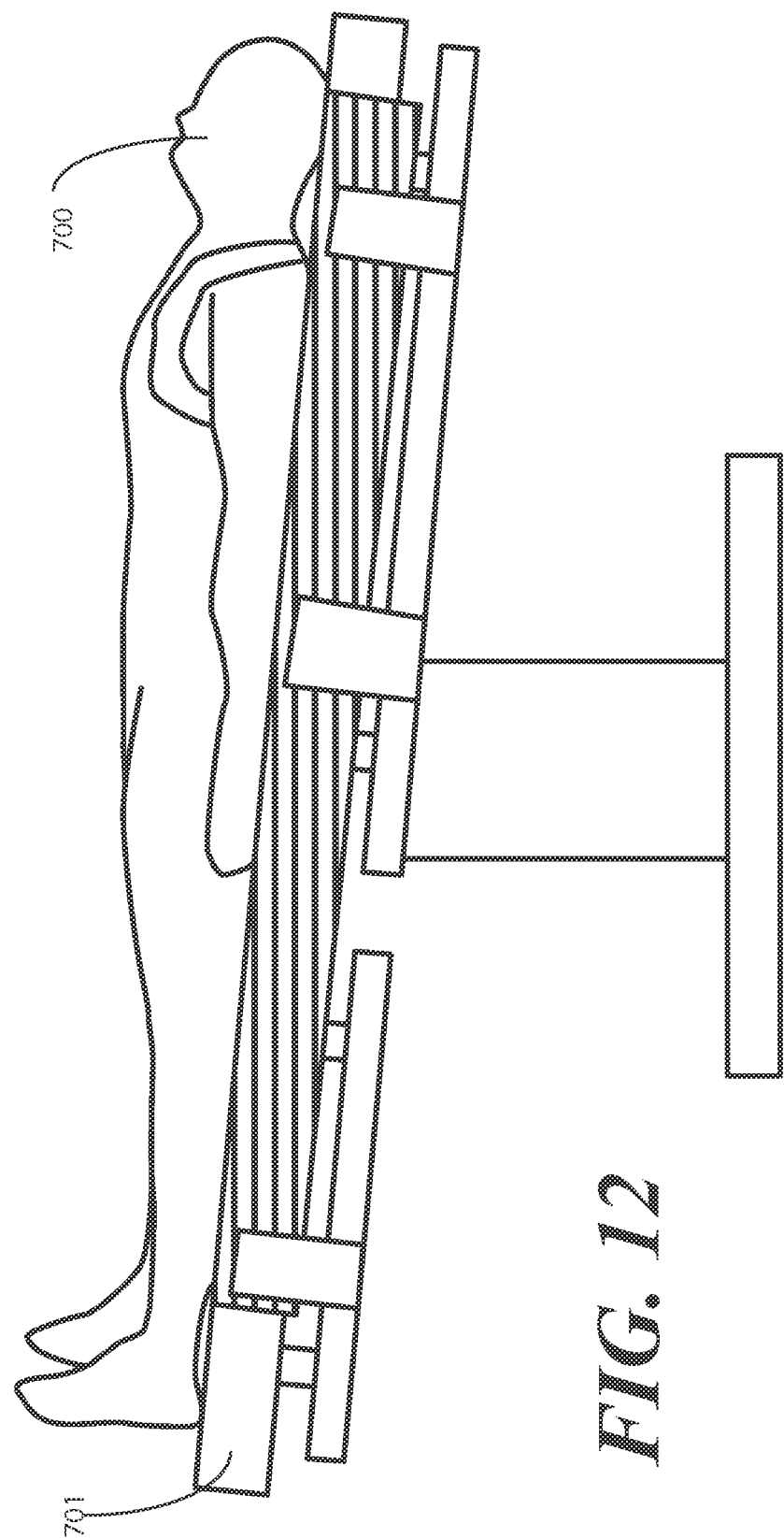
FIG. 12 illustrates a side elevation view of a patient on a procedure table being supported by an explanatory patient positioner configured in accordance with one or more embodiments of the invention.

One advantage offered by the embodiment of FIGS. 8 and 9 is that the patient need not worry about securement straps dangling from the patient positioner 800. Instead, as shown in FIG. 10, the holding layer 900 can first be attached to a procedure table 701. The patient can then don the patient positioner (800) and, as shown in FIG. 12, be placed along the holding layer 900 on the procedure table 701. As the area of fastener material (880) and the another area of fastener material 902 are complementary, the patient 700 is securely affixed to the procedure table 701. As shown in FIG. 13, the procedure table 701 can then be placed in the Trendelenburg position without fear of the patient 700 moving.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A patient positioner, comprising:
   a central portion;
   a pair of shoulder restraints extending distally from a first side of the central portion, each shoulder restraint terminating at an attachment area comprising a fastener;
   a pair of fasteners, each being complementary to the fastener, each disposed along the first side, and further disposed along a second and third side of the central portion, respectively; and
   a plurality of securement straps configured to attach the patient positioner to a procedure table and extending distally from the second side and the third side of the central portion, respectively;
   wherein the central portion defines a patient warming sensor insertion aperture.

2. The patient positioner of claim 1, wherein the patient positioner comprises a Trendelenburg positioner.

3. The patient positioner of claim 1, wherein each attachment area extends substantially orthogonally away from its corresponding shoulder restraint.

4. The patient positioner of claim 3, wherein the fastener is disposed on a patient side of the patient positioner.

5. The patient positioner of claim 4, wherein the pair of fasteners are disposed on a procedure table side of the patient positioner.

6. The patient positioner of claim 5, wherein the fastener comprises one of hook or loop fasteners and the pair of fasteners each comprise another of the hook or loop fasteners.

7. The patient positioner of claim 1, wherein the central portion comprises a padded layer disposed between two cover layers.

8. The patient positioner of claim 1, wherein each shoulder restraint of the pair of shoulder restraints is separated by a concave curvature disposed along the first side.

9. The patient positioner of claim 8, wherein a first edge of the each shoulder restraint comprises a substantially straight extension of the second side and the third side of the central portion, respectively.

10. The patient positioner of claim 9, wherein a second edge of the each shoulder restraint comprises an arch extending from the concave curvature to its corresponding attachment area.

11. The patient positioner of claim 1, wherein each securement strap comprises both hook and loop fasteners.

12. The patient positioner of claim 1, wherein each securement strap comprises a buckle.

13. The patient positioner of claim 1, wherein the plurality of securement straps comprise at least three securement straps extending from the second side and at least three additional securement straps extending from the third side.

14. The patient positioner of claim 1, wherein each fastener is attachable to its complementary fastener when a corresponding shoulder restraint is folded along a patient side of the central portion and a corresponding attachment area is folded around one of the second side or the third side to a procedure table side of the central portion.

15. The patient positioner of claim 1, wherein the each shoulder restraint is about thirty inches in length; and the central portion is about twenty inches wide.

16. A method of positioning a patient, comprising:
    passing a patient warming sensor through an aperture in a patient positioner and attaching the patient warming sensor to a patient's backside;
    placing the patient positioner along the patient's backside;
    folding a first shoulder restraint about a patient's first shoulder;
    wrapping a first attachment area extending from the first shoulder restraint about a first edge of the patient positioner to attach it to a side of the patient positioner facing away from the patient's backside;
    folding a second shoulder restraint about a patient's second shoulder; and
    wrapping a second attachment area extending from the second shoulder restraint about a second edge of the patient positioner to attach it to the side of the patient positioner facing away from the patient's backside.

17. The method of claim 16, further comprising:
    attaching the patient positioner to a procedure table; and
    placing a patient's body in a Trendelenburg position.

* * * * *